United States Patent [19]
Mance

[11] Patent Number: 5,257,969
[45] Date of Patent: Nov. 2, 1993

[54] ANKLE FOOT DORSIFLEXOR/SUPPORTER

[76] Inventor: Cornelius J. Mance, 5309 Inlet View La., Hixson, Tenn. 37343

[21] Appl. No.: 962,350

[22] Filed: Oct. 16, 1992

[51] Int. Cl.5 ............................................. A61F 5/00
[52] U.S. Cl. ...................................... 602/28; 602/30; 36/8.3
[58] Field of Search .................. 602/4, 11, 23, 27, 28, 602/30, 31; 128/880; 36/8.3, 95, 96; 2/239; 482/79

[56] References Cited

U.S. PATENT DOCUMENTS

| | | | |
|---|---|---|---|
| 1,659,171 | 2/1928 | Spafford | 2/239 X |
| 2,110,890 | 3/1938 | Paul | 36/8.3 |
| 2,703,405 | 3/1955 | Smallberg, Sr. | 2/239 |
| 2,816,541 | 8/1956 | Schultz | |
| 3,487,830 | 1/1970 | Pruett | 2/239 |
| 3,492,674 | 2/1970 | Poole | 2/239 |
| 3,986,501 | 10/1976 | Schad | |
| 4,166,460 | 9/1979 | Applegate | |
| 4,559,934 | 12/1985 | Philipp | |
| 4,621,648 | 11/1986 | Ivany | |
| 4,644,940 | 2/1987 | Nakamura | 602/30 |
| 4,817,589 | 4/1989 | Wertz | |
| 4,998,722 | 3/1991 | Scott | 482/79 |

Primary Examiner—Richard J. Apley
Assistant Examiner—Linda C. M. Dvorak

[57] ABSTRACT

A foot support will assist individuals with weakness or paralysis of dorsiflexion and eversion of the foot and extension of the toes, the condition commonly referred to as "foot drop." The foot support has a quilted, cushioned center piece and pouch forming a pocket for receiving the front of the user's foot. Straps affixed to each side of the quilted cushioned center piece extend across the dorsum of the user's foot, beneath the ankle and then around the distal to mid-leg of the user where they are secured by hook-and-loop fasteners. The foot support is sufficiently thin such that it can be positioned within the user's shoe.

20 Claims, 2 Drawing Sheets

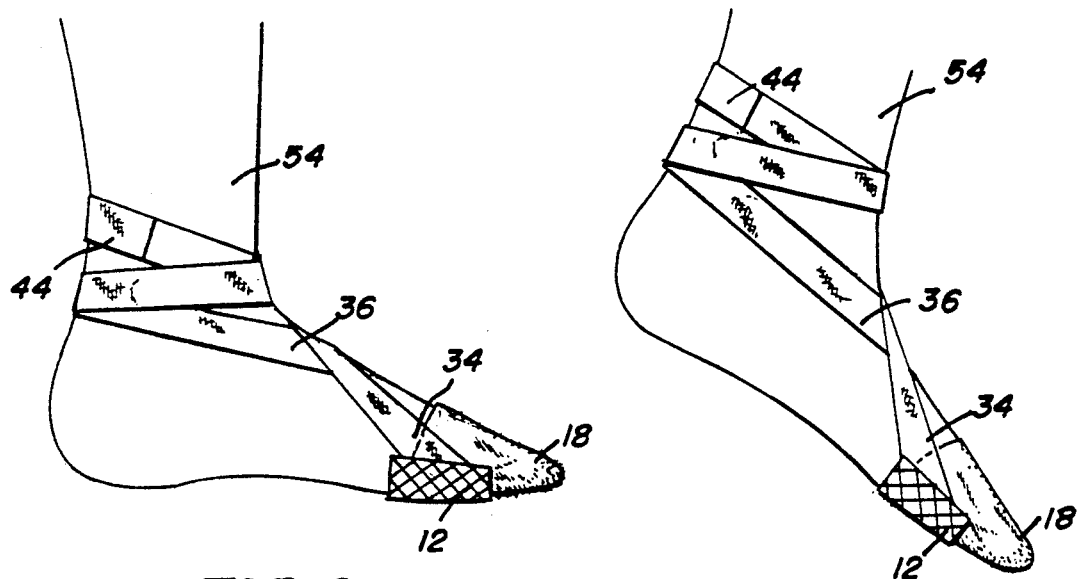
FIG. 4
FIG. 5
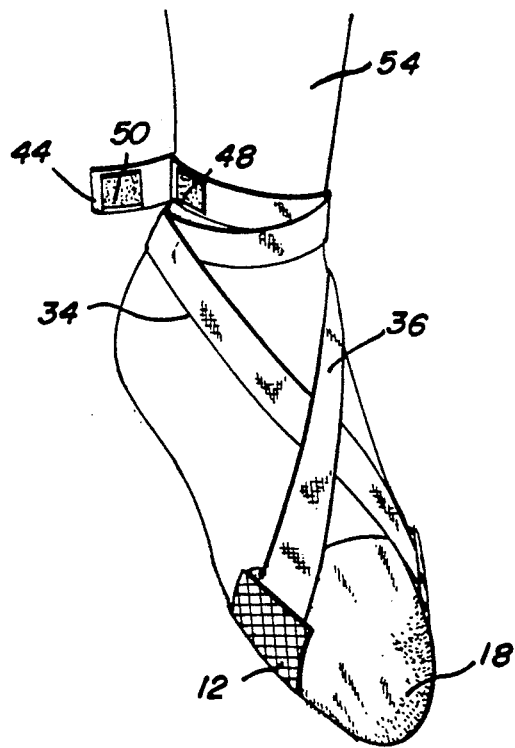
FIG. 6

ANKLE FOOT DORSIFLEXOR/SUPPORTER

BACKGROUND OF THE INVENTION

1. Field of the Invention

The present invention relates to a foot support which will assist individuals with weakness or paralysis of dorsiflexion and eversion of the foot and extension of the toes, the condition commonly referred to as "foot drop." The foot support comprises a quilted cushioned center piece with a pouch affixed thereto for receiving the forward end of the foot of the user. On the sides of the cushioned center piece are two straps which will wrap around the leg of a user.

2. Description of the Background Art

Foot drop is characterized in a person who otherwise has sufficient muscular control to move his or her foot relative to the ankle in planar flexion (a downward pushoff motion), lacks sufficient muscular control to subsequently affect a dorsiflexion motion to raise the foot back up for the next step. Also, usually evidenced in a person's having foot drop is the diminished capacity to move the foot in what is termed eversion, or rotating the outer part of the foot in an upward manner.

Two central disorders of gait which can benefit from the instant foot support are gait hemiparesis and gait paraparesis. The hemiparetic patient typically stands and walks with the affected arm flexed and the leg extended. In walking, the patient has difficulty flexing the hip and knee, dorsoflexing the ankle and everting the foot. The paretic leg swings outward at the hip with the trunk rocking in the opposite direction to avoid scraping the toes of the foot on the floor. The leg rotates in a semicircle, first away from and then towards the trunk. This attempts to prevent the foot from scraping the floor which would cause the toe and inner side of the sole of the shoe to be worn first.

Similarly, the spastic paraparetic gait has some problem with walking as the hemiparetic patient, but bilaterally. Their steps are short but the patient rocks the trunk side-to-side trying to compensate for the inability to flex hips and stiff-leg movement. The feet scrape the floor; therefore, the soles of the shoe at the toes are immediately worn.

The common peroneal nerve is the continuation of a lateral trunk of the sciatic nerve which is derived from the posterior division of the vertical rami of spinal nerves L4, L5, S1 and S2 (primarily L4, L5, S1). This nerve usually separates from the sciatic nerve in the upper popliteal fossa (into the common peroneal nerve and tibial nerve). The common peroneal nerve descends downwardly and laterally in the popliteal fossa, passing behind the head of the fibula and winds obliquely around its neck. This nerve then pierces the superficial head of the peroneus longus muscle which forms a tendinous arch over the nerve (fibular tunnel) and as it emerges from the tunnel, it divides into two major branches (1) superficial peroneal (musculocutaneous) and (2) deep (anterior tibial), peroneal nerves. The deep peroneal nerve runs in the anterior compartment of the leg between the anterior tibialis and extensor hallucis muscles and tendons, which innervates the (1) anterior tibialis, (2) extensor hallucis brevis and longus, extensor digitorum longus and brevis and peroneus tertius muscles.

The function of each muscle innervated by the deep peroneal nerve is as follows. The anterior tibialis carriers out dorsiflexion of the ankle joint and inversion of the foot. When weakened, it decreases the ability to dorsiflex the ankle joint and allows a tendency towards eversion of the foot.

The extensor hallucis longus and brevis act to extend the metatarsophalangeal and interphlangal joints of the great toe. This assists in inversion of the foot and dorsiflexion of the ankle joint. If weakened, it will decrease the ability to extend the great toe and allows a position of flexion. The ability to dorsiflex the ankle joint is decreased.

The extensor digitorum longus and bevis act to extend the metatarsophalangeal joints and assist in extending the interphalangeal joints of the second through fifth digits and second through fourth digits. When weakened, it will decrease the ability to dorsiflex the ankle joint and evert the foot.

The peroneus tertius acts to dorsiflex the ankle joint and everts the foot. If weakened, it will decrease the ability to evert the foot and dorsiflex the ankle joint.

A complete lesion of the common peroneal nerve results in the classic foot drop, i.e. the inability of dorsiflexion and eversion of the foot and extension of the toes and a slapping gait. This disorder can be caused by strokes, spastic paraparesis, polio, amyotrophic lateral sclerosis, multiple sclerosis and parkinsonism. Peripheral causes of palsy of the common peroneal nerve are external compression, direct trauma, traction injuries, masses, entrapment, vascular, diabetes, leprosy, lumbosacral trunk injury, sciatic nerve injuries or neuropathies secondary to Guillian-Barre, toxic metabolic or alcohol.

While other prior art devices have attempted to address the problem of foot drop, there have been many drawbacks with these devices. Often they are bulky, heavy and cumbersome. Due to their weight, they will unnecessarily fatigue the user and will be uncomfortable. Some of these devices will excessively confine the leg and place limitations on the foot and ankle movement which tends to further reduce the remaining functional capacity of the patient. Therefore, these devices can hinder the patient's ability.

Some prior art devices cannot be used without professional aid. Also, many devices require orthopedic shoes or other specialized shoes. A user cannot walk barefoot or with sandals or slippers in such devices.

An additional drawback to many prior art devices is that they are visible such that they draw attention to the patient's problem. This is psychologically difficult for a user who is often self-conscious of his or her condition.

Many prior art arrangements require an excessive attachment arrangement. For older users who might have arthritis, these devices are unacceptable.

Accordingly, a need in the art exists for a simple and effective foot support which will assist individuals with weakness or paralysis of dorsiflexion and eversion of the foot and extension of the toes. This device should be easy to put on, lightweight and nonconspicuous.

SUMMARY OF THE INVENTION

Accordingly, it is a primary object of the present invention to provide a foot support which is not heavy, bulky or cumbersome.

It is another object of the present invention to provide a foot support which can be hidden from view and which is not conspicuous.

It is a further object of the present invention to provide a foot support which does not excessively confine the leg.

Yet another object of the present invention is to provide a foot support which can be used without professional aid, and which is simple to put on.

Yet a further object of the present invention is to provide a foot support which does not require special shoes.

A further object of the present invention is to provide a foot support which is comfortable to wear and will not excessively tire the user.

A further object of the present invention is to provide a device which is easy to clean and requires limited to no maintenance.

A further object of the present invention is to provide a device which is simple and inexpensive to manufacture.

These and other objects of the present invention are fulfilled by providing a foot support which has a quilted cushioned center piece and a pouch affixed thereto. The pouch can be a composition of reinforced sock-like material. An elastic strap is provided on each side of the center piece. This elastic strap will extend across the user's foot, around their ankle and then be wrapped around their leg where the straps can be secured by hook-and-loop fasteners. The foot support is sufficiently thin and flexible such that it can be placed within a user's shoe.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 4 is a side view of the foot support of the instant invention with the user's foot raised;

FIG. 5 is a side view of the foot support of the present invention with the user's foot extended; and FIG. 6 is a perspective front view of the foot support of the instant invention showing the straps crossed over the user's instep.

DETAILED DESCRIPTION OF THE PREFERRED EMBODIMENTS

Figure 1:
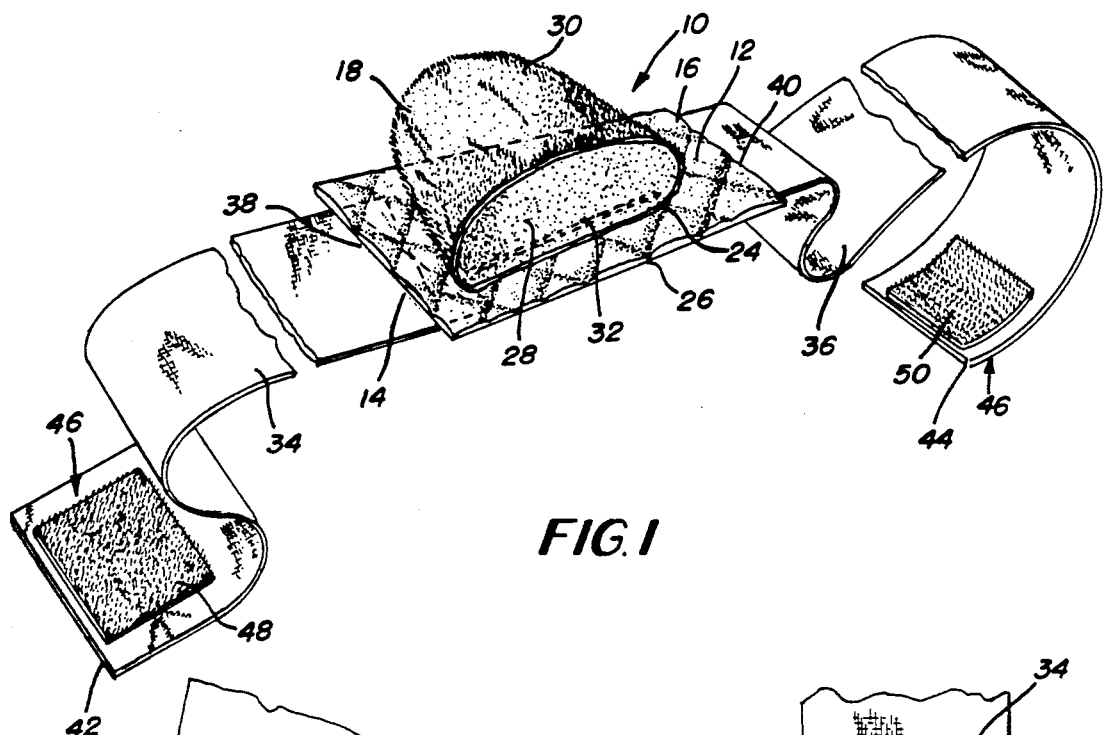
FIG. 1 is a perspective top view of the foot support of the present invention.
Figure 3:
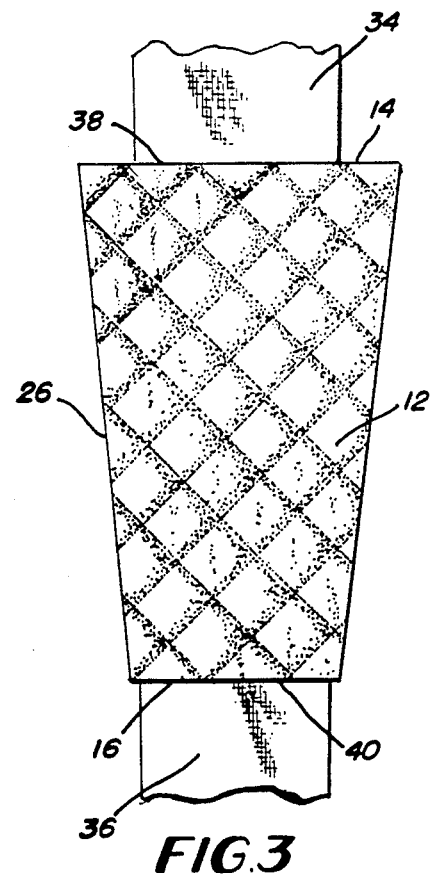
FIG. 3 is a plan view of the quilted cushioned center piece of the present invention.

Referring in detail to the drawings and with particular reference to FIG. 1, a foot support 10 is shown. This foot support 10 comprises a quilted cushioned center piece 12. The cushion piece 12 has a trapezoidal shape as shown in FIG. 3. The rear side 14 of this piece 12 is slightly larger than the front side 16. For example, the rear side 14 can be about three inches while the front side 16 can be two and one-half inches. The length of this piece 12 can be five to seven inches, for example.

This trapezoidal shape of the piece 12 helps the foot support 10 conform to the shape of the user's foot. It should be recognized that the quilted cushioned center piece 12 can be made generally rectangular if so desired. This piece 12 is readily interchangeable between the feet of a user. Also, the quilted cushioned piece can be positioned within pouch 18 or can be used with a pouch having only a top and sides, but no bottom. It is, therefore, possible to turn the quilted cushioned piece 12 and pouch 18 inside out.

The quilted cushioned center piece 12 is merely a quilted piece of cloth. This quilted cushioned center piece 12 is flexible. On the upper side of the cushion piece 12, a pouch 18 is affixed. This pouch 18 will conform to the shape (trapezoidal, rectangular, etc.) of the cushion piece 12. The pouch 18 shown in FIG. 1 is attached to the quilted cushion center piece 12. Within this pouch 18, a pocket 28 is formed for the forward end of the user's foot. This pouch 18 is made from a piece of cloth, such as a reinforced sock-like material. It should be appreciated that the pouch 18 and cushion piece 12 can be sized to accommodate different size feet. Moreover, because these pieces are flexible, one size foot support 10 can fit most feet.

In FIG. 1, the pouch 18 has a top side 30 and lower side 32. The lower side 32 can be omitted (as noted above), such that the pouch 18 and top 26 of the cushion piece 12 will form the pocket 28. However, when the lower side 18 of the pouch is provided and is attached to quilted cushioned piece 12, this design will allow for increased flexibility so that one size fits all.

It is preferred that the quilted cushioned center piece 12 is sewn along the lower side 32 to the pouch 18. Alternatively, any means for attaching the pouch 18 to the cushion piece 12 is acceptable. For example, the pouch 18 can be glued to the cushion piece.

FIG. 1 shows the forward edge 24 of the pouch 18 spaced from the rear edge 14 of the quilted cushioned piece 12. The pouch 18 can be slightly larger than shown relative to the cushion piece 12 such that it overhangs this piece 12. Alternatively, the cushion piece 12 can be made even larger than shown relative to the pouch 18 or the cushion piece 12 and the pouch 18 can be the same size. Many different combinations are possible. It is merely necessary that the forward end of the foot of a user can be placed within the pocket 28 formed by pouch 18 (or by pouch 18 and cushion piece 12).

The contoured pouch 18 will fit the toes of the user. The forward end of a user's foot is inserted into the pocket 28. The cushion piece 12 will have a contour fit on the first to fifth metatarsophalangeal joints (ball of the foot) or any other suitable location of the user's foot.

FIG. 1 further shows two straps 34, 36. The first ends 38, 40 of straps 34, 36, respectively, are attached to the outer sides of cushion piece 12. These straps extend, generally, straight out from the sides of the quilted cushioned piece 12. The straps 34, 36 can be sewn or otherwise affixed to the sides of this cushion piece 12. As shown in FIG. 1, the ends 38, 40 are sewn inside quilted cushioned piece 12. This helps to cushion the effects of the added thickness of the straps. Alternatively, the ends 38, 40 of the straps can be positioned beneath the cushion piece 12, between the cushion piece 12 and the pouch 18 or affixed to the pouch 18.

The second ends 42, 44 of straps 34, 36 have a fastener 46. This fastener 46 can be a Velcro ™, hook-and-loop fastener or any other suitable fastening means. For example, snaps, clips, buckles or other means can be used as the fastener 46. Either the hook or loop portion 48 is placed on end 42 while the other fastener portion 50 will be placed on end 44. As will be discussed in more detail below, the hook-and-loop fasteners will be positioned in mating configuration in use such that the foot support 10 will be held in position.

Figure 2:
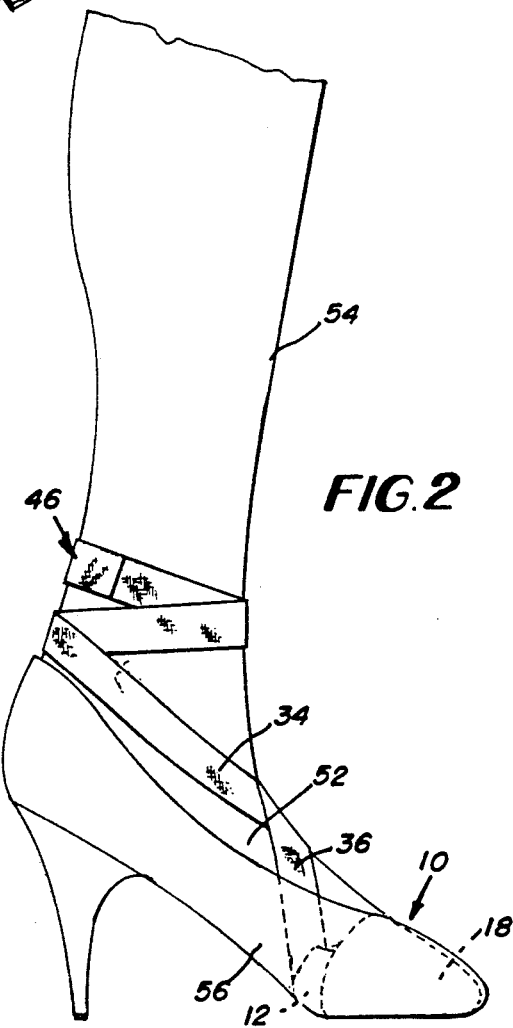
FIG. 2 is a side view of the foot support of the present invention within a user's shoe.

Turning now to FIG. 2, a user's foot 52 and leg 54 are shown. As will be described below, the foot support 10 of the instant invention is sufficiently thin such that it can be positioned within the shoe 56 of the user. To prevent pressure or irritation to the user's foot or leg, the support 10 should be worn with the sock or stocking. The quilted cushioned piece 12 is positioned beneath the first to fifth metatarsophalangeal joints (ball of foot) as noted above. The pouch 18 will receive the forward end of the user's foot.

In FIG. 2, strap 34 is simply wrapped around the foot 52 and leg 54 in mirror image to the first strap 36. The strap 36 shown in FIG. 2 extends rearwardly from the cushion piece 12. This strap crosses the dorsum of the user's foot, then extends below the ankle (at or just above the medial and lateral malleoli), then wraps around the distal to mid-leg (fibula and tibia) where the strap 36 will be secured by the hook-and-loop fastener 46 to the other strap 34. In other words, the straps 34, 36 emerge from the shoe 56, shown in FIG. 2, and immediately cross over the instep of the foot. The straps are kept sufficiently low, to go just under the ankle bone. The next wrap is nearly horizontal, and the final wrap is at a slightly higher angle before hooking the fastener 46. While fastener 46 is shown on one side of the user's leg 54, it should be appreciated that this location can be varied. For example, the fastener 46 can be located at the back of the user's leg 54.

The total length of the device of the instant invention can be approximately forty-nine inches. Each strap can be about twenty-two inches long and about two inches wide. The hook-and-loop fasteners 48, 50 can each be about an eight inches long and one inch wide strip. These noted dimensions are merely exemplary.

The straps 34 and 36 are made from elastic (tightly woven) material or reinforced with rubber straps. They can accommodate movement of the foot as shown in FIG. 5 (where straps 34, 36 are slightly stretched), but will generally hold the foot 52 in the position as shown in FIG. 4. The straps 34 and 36 with the fastener, however, act as a lift means to lift the foot in pocket 28. Therefore, the instant foot support 10 will assist individuals with weakness or paralysis of dorsiflexion and eversion of the foot and extension of the toes. The support 10 will also give support to the ankle.

While FIG. 2 indicates the foot support 10 as being provided within a user's shoe, it should be recognized that this device can be used without a shoe or, if so desired, can be positioned on the outside of the user's shoe. Under such conditions, the support 10 will need to be made from a more durable material. Therefore, there is great flexibility with the instant device.

The quilted cushioned center piece 12 and pouch 18 are made from cloth and the straps 34, 36 are made from elastic material. Therefore, all of the foot support 10 of the instant invention is flexible. A very lightweight and comfortable arrangement is obtained.

To place the foot support 10 on the user's foot, it is simply necessary to slip the user's toes into pocket 28. Then the straps are wound across the dorsum of the foot, around the leg and then fastened together with hook-and-loop fastener 46. An older user or a person with arthritis will find this foot support extremely easy to use. No cumbersome buckling is necessary when using the instant foot support.

The instant foot support is very lightweight. It will therefore not tire the user and will be comfortable to wear. Because it is adjustable, different tensions can be placed on the straps.

The instant foot support 10 requires no special shoes, no orthopedic shoes and, in fact, can be worn without shoes as noted above. Therefore, the user can wear sandals, slippers or walk around barefoot or in sock feet. When in public, the foot support 10 can be hidden within the shoe and pants or dress of the user. Therefore, this device is hidden from view and is less conspicuous than other prior art devices. Moreover, the straps do not extend a great distance up the leg 54 of the user. The user will not be self-conscious when using the instant foot support, thereby having great psychological benefits.

The foot support 10 is washable and easy to maintain. In fact, this foot support can be machine washed so that little care is required. Otherwise, limited to no maintenance is required for the instant foot support 10.

This foot support is reusable and can be put on without professional assistance. The foot support 10 is simple and inexpensive to manufacture and comfortable to wear.

The instant foot support will act as an ankle foot dorsiflexor/supporter which will serve the functions of assisting dorsiflexion of the ankle and foot, assisting inversion and eversion of the foot and assisting extension of the metatarsophalangeal joints of the first through fifth digits. This foot support will also assist extension of the interphalangeal joints of the second through fifth digits. Further, the foot support will act as an ankle support.

Many advantages are had with the foot support of the instant invention. The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A foot support device for assisting a user with weakness or paralysis of dorsiflexion and eversion of the foot, the foot support device comprising:
   a cushion piece;
   a pouch affixed to the cushion piece and forming a pocket, the pouch having an opening through which a forward end of a foot is insertable so that the pocket is for receiving a forward end of a foot, the pouch adjacent the opening having a continuous, unbroken edge, the edge extending at least from a first side of the pouch adjacent the cushion piece, over a top of the pouch and to a second side of the pouch adjacent the cushion piece, the continuous, unbroken edge of the pouch generally having an arch shape from the first side to the second side of the pouch, the cushion piece and pouch being a cloth material; and
   lift means for lifting the foot in the pocket, the lift means comprising two elastic straps and a fastener device, each strap having first and second ends, one of each of the first ends of the straps being affixed to each side of the cushion piece, the sides of the cushion piece to which the straps are affixed being spaced outwardly of the pouch such that the pouch is between the sides of the cushion piece having the straps affixed thereto, each strap having a length sufficient to extend from the cushion piece, across the user's foot, around an ankle of the user and then to wrap around a leg of the user such that the second ends of the straps overlie one another, the fastener device detachably affixing the two second ends overlying one another to thereby hold the straps in position.

2. The foot support device as recited in claim 1, wherein the cushion piece is a piece of quilted cloth material.

3. The foot support device as recited in claim 1, wherein the cushion piece has a trapezoidal shape.

4. The foot support device as recited in claim 1, wherein all of the device is flexible.

5. The foot support device as recited in claim 1, wherein a rearward side of the pouch is affixed to a forward end of the cushion piece.

6. The foot support device as recited in claim 5, wherein the pouch and the first ends of the straps are sewn to the cushion piece.

7. The foot support device as recited in claim 1, wherein the fastener is a hook-and-loop fastener having mating portions on the second ends of the straps.

8. The foot support device as recited in claim 1, wherein the device has a thickness sufficiently thin to enable the device to be positioned within a user's shoe.

9. A foot support device for assisting a user with weakness or paralysis of dorsiflexion and eversion of the foot, the foot support device comprising:
   strap means for engaging both sides of a user's foot, for extending across the user's foot and for wrapping around a leg connected to the user's foot, the strap means includes two straps;
   a cushion piece having first and second sides, each of the sides being affixed to one end of each of the straps; and
   pouch means affixed to the cushion piece defining a pocket for receiving a forward end of the user's foot, the pouch means being positioned inwardly of the first and second sides of the cushion piece and being between the ends of the straps, the cushion piece and pouch means both being a cloth material, the pouch means having an opening through which the forward end of the user's foot is inserted, the pouch means further having a continuous, unbroken edge adjacent the opening and having a first side and a second side, the first side of the pouch means being adjacent the first side of the cushion piece and the second side of the pouch means being adjacent the second side of the cushion piece, the edge of the pouch means extending at least from the first side of the pouch means, over a top of the pouch means and to the second side of the pouch means, the continuous, unbroken edge of the pouch means generally having an arch shape from the first side to the second side of the pouch means,
   whereby the foot support device on a user's foot will lift and support the foot.

10. The foot support device as recited in claim 9, further comprising means enabling the foot support device to be positioned between a shoe of the user and the user's foot, the means comprising the strap means, cushion piece and pouch means being sufficiently thin and flexible to be accommodated within the user's shoe.

11. The foot support device as recited in claim 9, further comprising means for detachably affixing the two straps to one another in an area of the leg of the user.

12. The foot support device as recited in claim 11, wherein the means for detachably affixing comprises mating hook-and-loop fasteners affixed to ends of the two straps opposite to the end affixed to the cushion piece.

13. The foot support device as recited in claim 9, wherein the cushion piece has a trapezoidal shape.

14. The foot support device as recited in claim 9, wherein all of the device is flexible.

15. The foot support device as recited in claim 9, wherein a lower forward side of the pouch means is affixed to the cushion piece.

16. The foot support device as recited in claim 9, wherein the device has a thickness sufficiently thin to enable the device to be positioned within a user's shoe.

17. The foot support device as recited in claim 9, wherein the cushion piece is a piece of quilted cloth material.

18. A method of assisting users with weakness or paralysis of dorsiflexion and eversion of the foot, comprising the steps of:
   providing a cushion piece with a pouch affixed thereto, the cushion piece and pouch forming a pocket;
   inserting a forward end of the foot into the pocket;
   enclosing the forward end and toes of the foot by the pouch as a result of the step of inserting, a rearward end of the foot failing to be enclosed by the pocket;
   providing at least one elastic strap and a fastener device, the at least one elastic strap being affixed to the cushion piece;
   wrapping the at least one elastic strap across the foot, around an ankle and around a leg of the user;
   fastening the at least one elastic strap is position across the foot, around the ankle and around the leg, the at least one strap being operatively connected to both sides of the pouch after the step of fastening;
   lifting the foot in the pocket after the steps of inserting and fastening, the foot being lifted by the pocket and the at least one strap wrapped around the leg of the user, the foot being free to move relative to the leg of the user before the step of fastening so that an angle between the foot and user can change; and
   holding the foot at a predetermined angle relative to the leg after the steps of fastening and lifting, the at least one strap preventing the foot from dropping relative to the leg of the user during the step of holding.

19. The method as recited in claim 18, wherein two straps are provided as the at least one strap and wherein each strap has first and second ends, the first ends of the straps being affixed to opposed sides of the cushion piece and wherein the step of fastening further comprises the step of affixing the second ends of the straps together.

20. The method as recited in claim 18, further comprising the step of inserting the cushion piece and pouch into a user's shoe after the step of fastening.

* * * * *